United States Patent [19]
Wijesekera et al.

[11] Patent Number: 5,770,728
[45] Date of Patent: Jun. 23, 1998

[54] ALKANE OXIDATION WITH PORPHYRINS AND METAL COMPLEXES THEREOF HAVING HALOALKYL SIDE CHAINS

[75] Inventors: Tilak Wijesekera, Glen Mills; James E. Lyons, Wallingford; Paul E. Ellis, Jr., Downingtown; Manoj V. Bhinde, Boothwyn, all of Pa.

[73] Assignee: Sun Company, Inc. (R&M), Philadelphia, Pa.

[21] Appl. No.: 769,814

[22] Filed: Dec. 19, 1996

Related U.S. Application Data

[60] Division of Ser. No. 405,684, Mar. 17, 1995, Pat. No. 5,608,054, which is a continuation-in-part of Ser. No. 174,732, Dec. 29, 1993, Pat. No. 5,571,908, which is a continuation-in-part of Ser. No. 175,057, Dec. 29, 1993, abandoned.

[51] Int. Cl.⁶ .......................... C07D 487/22; C07C 45/32
[52] U.S. Cl. .......................................... 540/145; 568/399
[58] Field of Search ............................................. 540/145

[56] References Cited

U.S. PATENT DOCUMENTS

| | | | |
|---|---|---|---|
| 4,892,941 | 1/1990 | Dolphin et al. | 540/145 |
| 4,895,680 | 1/1990 | Ellis et al. | 540/145 |
| 4,895,682 | 1/1990 | Ellis et al. | 540/145 |
| 4,900,871 | 2/1990 | Ellis et al. | 568/399 |
| 4,910,349 | 3/1990 | Sanderson et al. | 568/909.8 |
| 4,912,266 | 3/1990 | Sanderson et al. | 568/909.8 |
| 4,922,034 | 5/1990 | Sanderson et al. | 568/909.8 |
| 4,970,348 | 11/1990 | Ellis et al. | 568/399 |
| 4,992,602 | 2/1991 | Sanderson et al. | 568/909.8 |
| 5,120,882 | 6/1992 | Ellis et al. | 568/910 |
| 5,120,886 | 6/1992 | Lyons et al. | 568/909.6 |
| 5,241,062 | 8/1993 | Wijesekera et al. | 540/145 |
| 5,371,199 | 12/1994 | Therien et al. | 534/11 |
| 5,599,924 | 2/1997 | Therien et al. | 540/145 |

FOREIGN PATENT DOCUMENTS 0 308 101   8/1988   European Pat. Off. .

OTHER PUBLICATIONS

Adler, et al., "On the Preparation of Metalloporphyrins", *J. Inorg. Nucl. Chem.*, 32, 2443 (1970).

Badger, et al., "Porphyrins VII. The Synthesis of Porphyrins by the Rothemund Reaction", *Aust. J. Chem.*, 17, 1028–1035 (1964).

DiMagno, et al., "Facile Synthesis of Meso–Tetrakis (Perfluoroalkyl) Porphyrins: Spectroscopic Properties and X–Ray Crystal Structure of Highly Electron–Deficient 5,10,15,20–Tetrakis (Heptafluoropropyl) Porphyrin." *J. Organ. Chem.*, 59, 23, 6943–6948 (1994).

Ellis, et al., "Halogen Substituent Effects on the Catalytic Activity of Iron Porphyrin Complexes for Selective Air–Oxidation of Alkanes in the Liquid Phase", *Cat. Lett.*, 3, 389 (1989).

Lindsey, et al., "Investigation of the Synthesis of Ortho–Substituted Tetraphenylporphyrins", *J. Organ. Chem.*, 54, 828 (1989).

Lyons, et al., "Selective Low Temperature Hydroxylation of Isobutene By Molecular Oxygen Catalyzed by an–Iron Perhaloporphyrin Complex", *Cat. Lett.*, 8, 45 (1991).

Lyons, et al., "Halogen Substituent Effects on the Catalytic Activity of Iron Porphyrin Complexes for the Decomposition of tert–Butyl Hydroperoxide", *J. Catalysis*, 141, 311 (1993).

Wagner, R.W., et al., "Building Block Synthesis of Linear–Amphipathic Porphyrin Arrays", *Meeting of Amer. Chem. Soc. Div. Organ. Chem.*, Mar. 13–17, 1994, San Diego, CA (poster abstract and paper).

*Primary Examiner*—Mukund J. Shah
*Assistant Examiner*—Pavanaram K. Sripada
*Attorney, Agent, or Firm*—Q. Todd Dickinson; Stephen T. Falk

[57] ABSTRACT

Transition metal complexes of meso-haloalkylporphyrins, wherein the haloalkyl groups contain 2 to 8 carbon atoms have been found to be highly effective catalysts for oxidation of alkanes and for the decomposition of hydroperoxides.

12 Claims, 7 Drawing Sheets

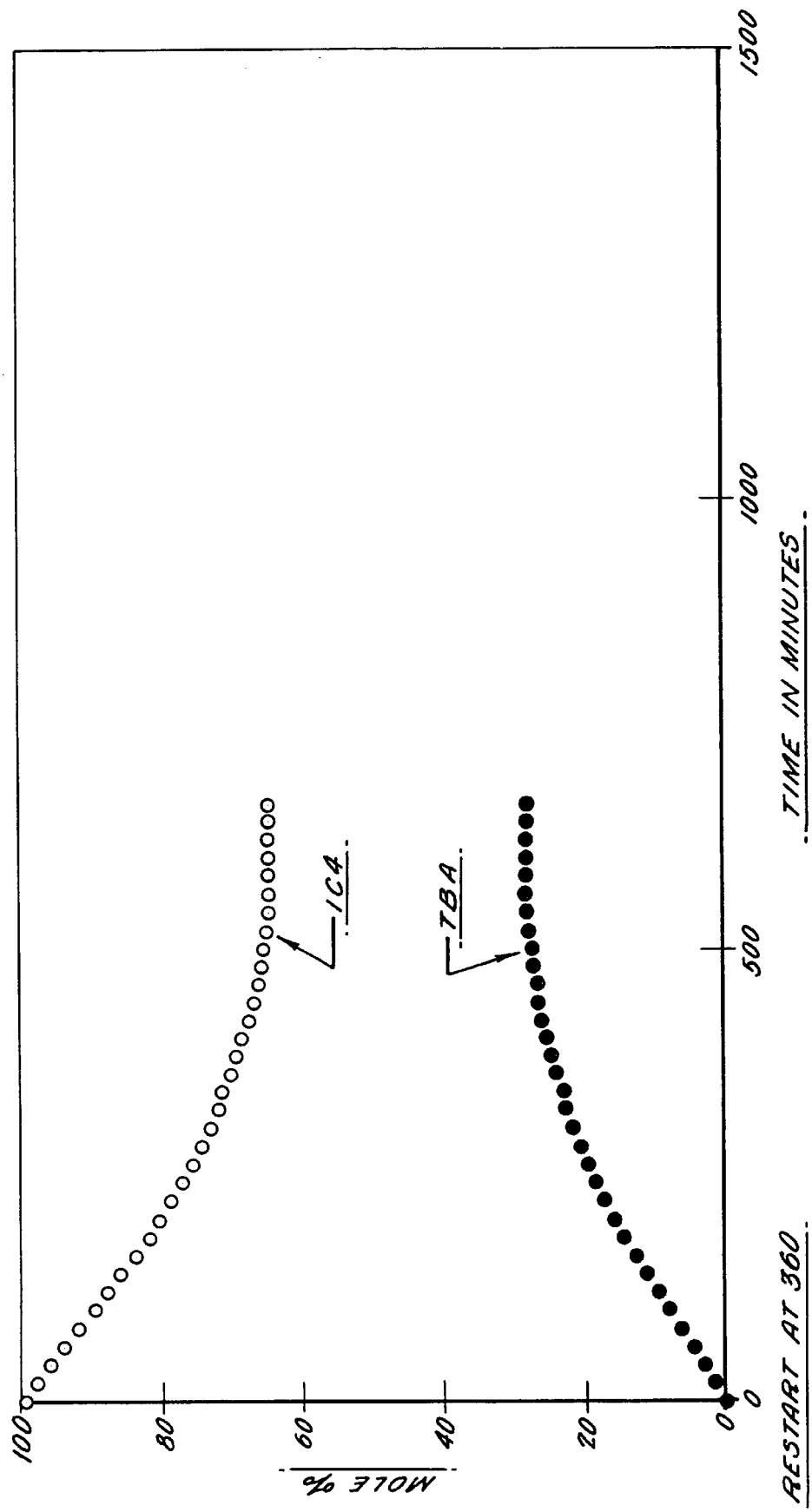

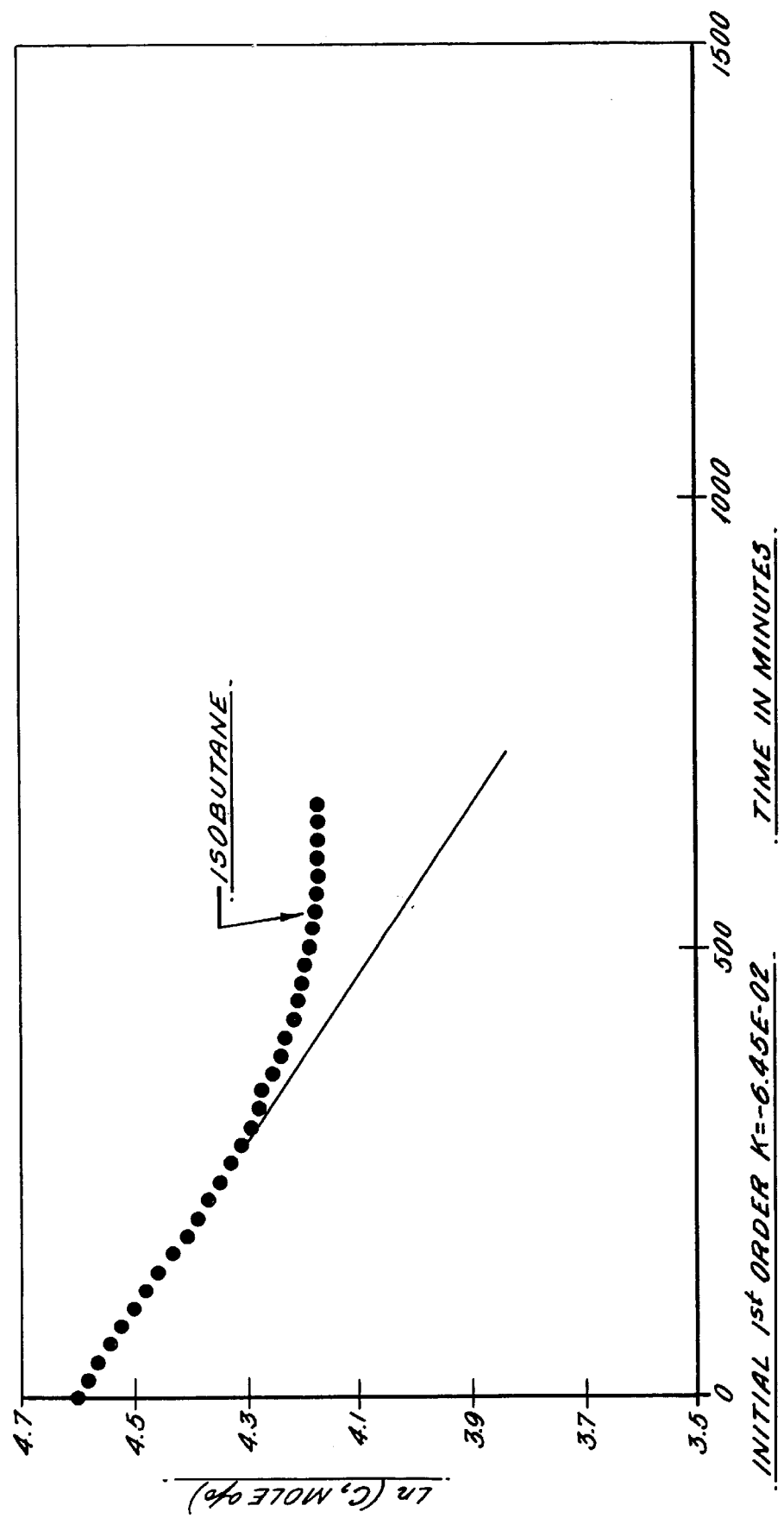

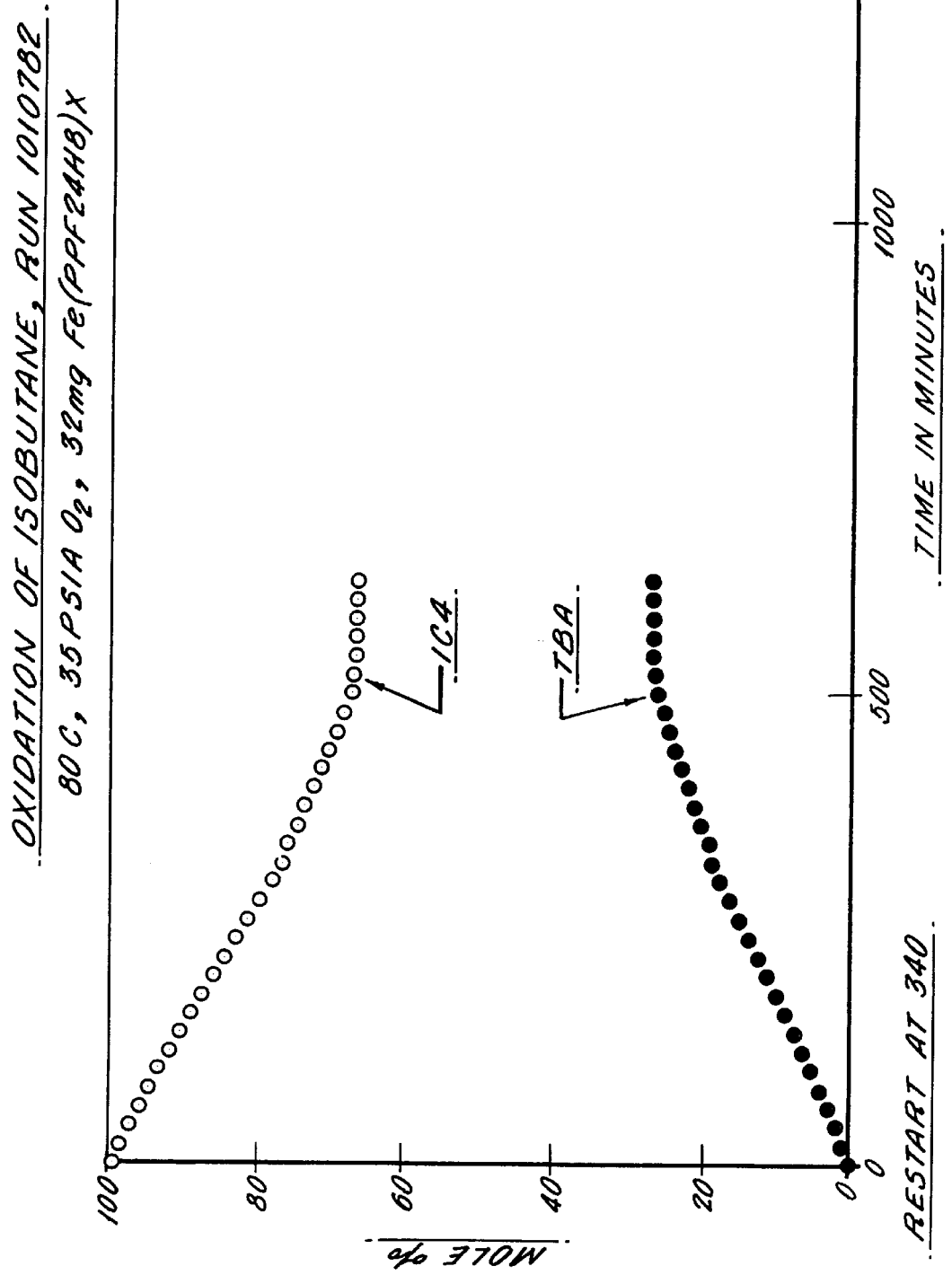

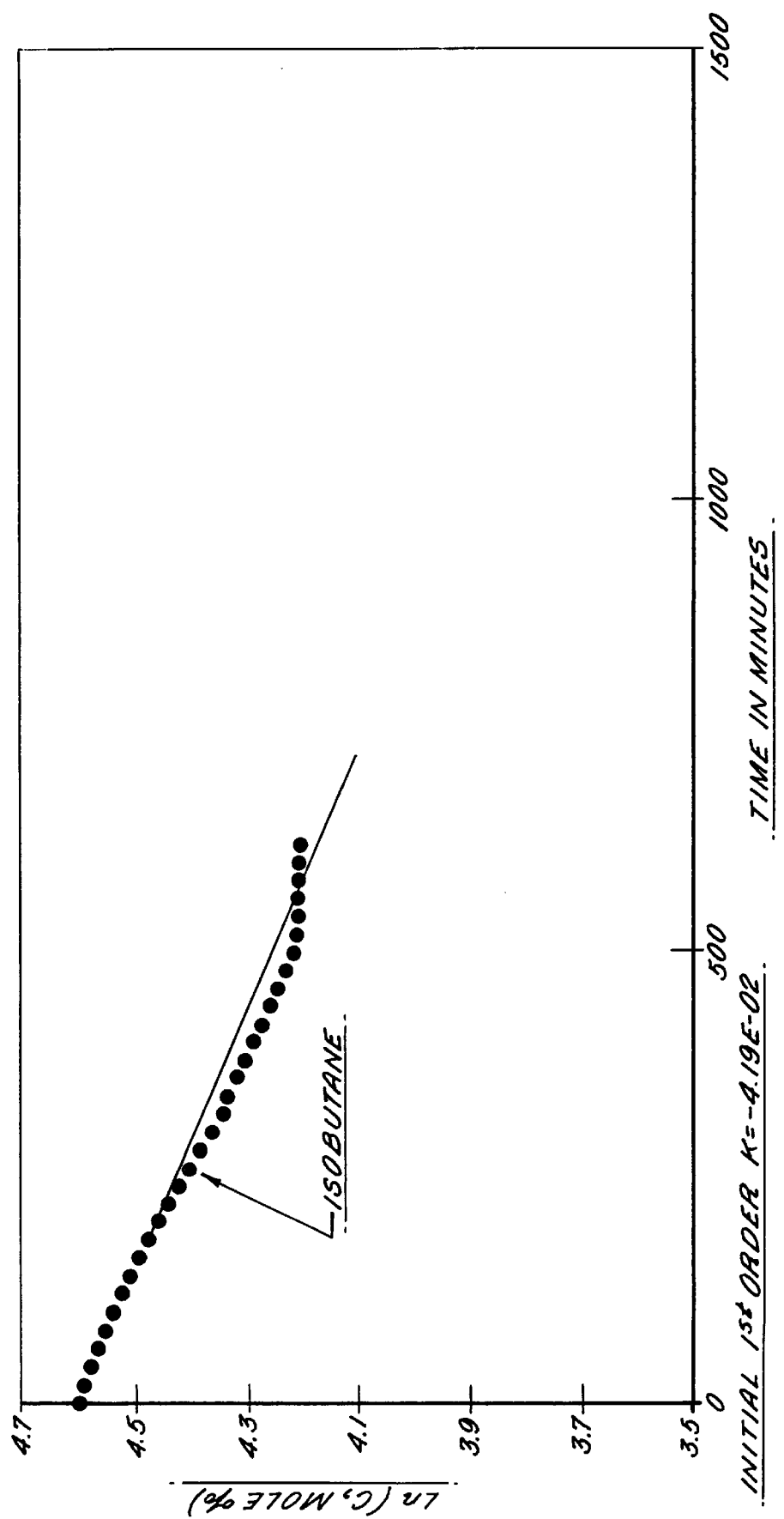

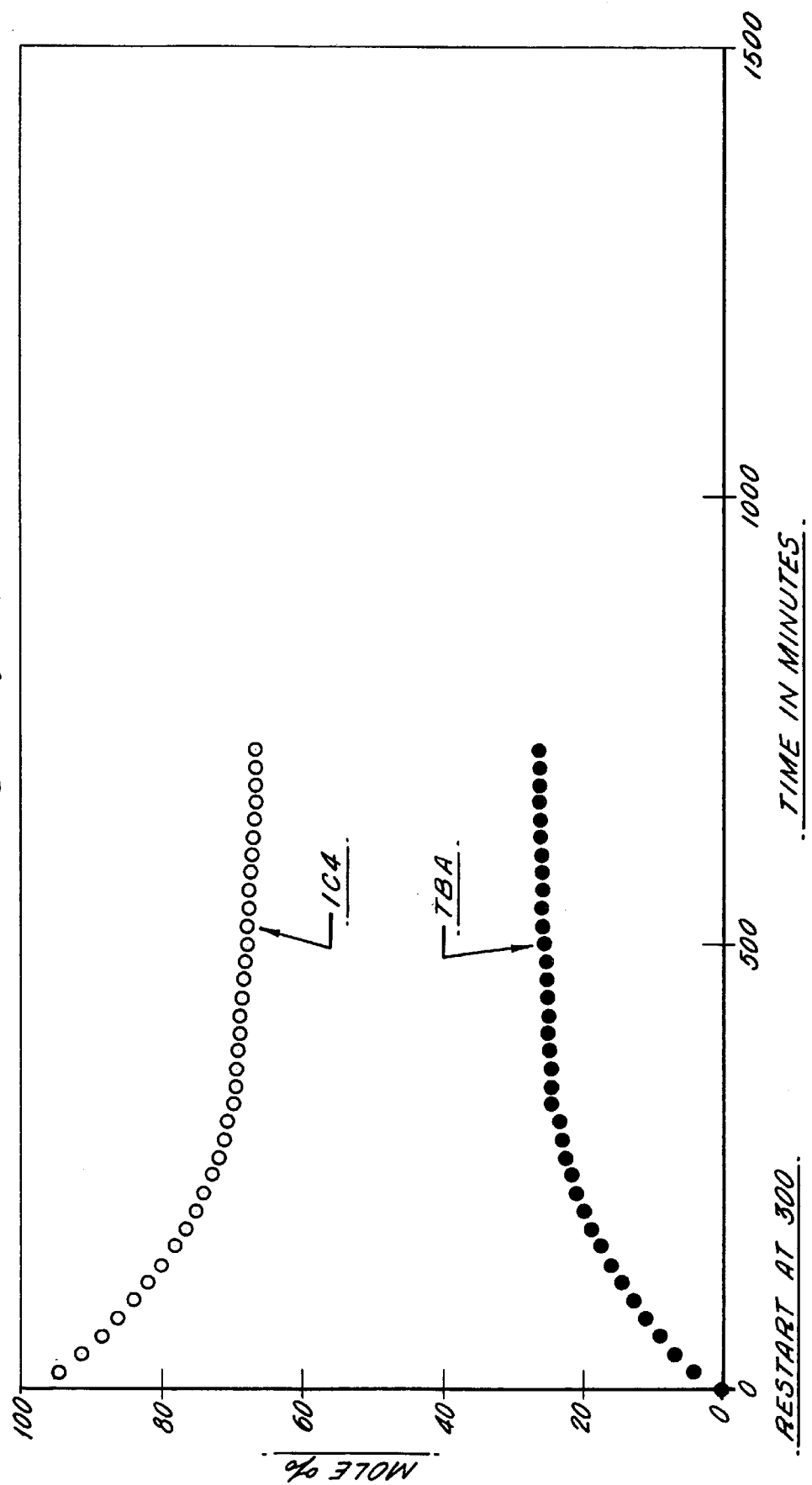

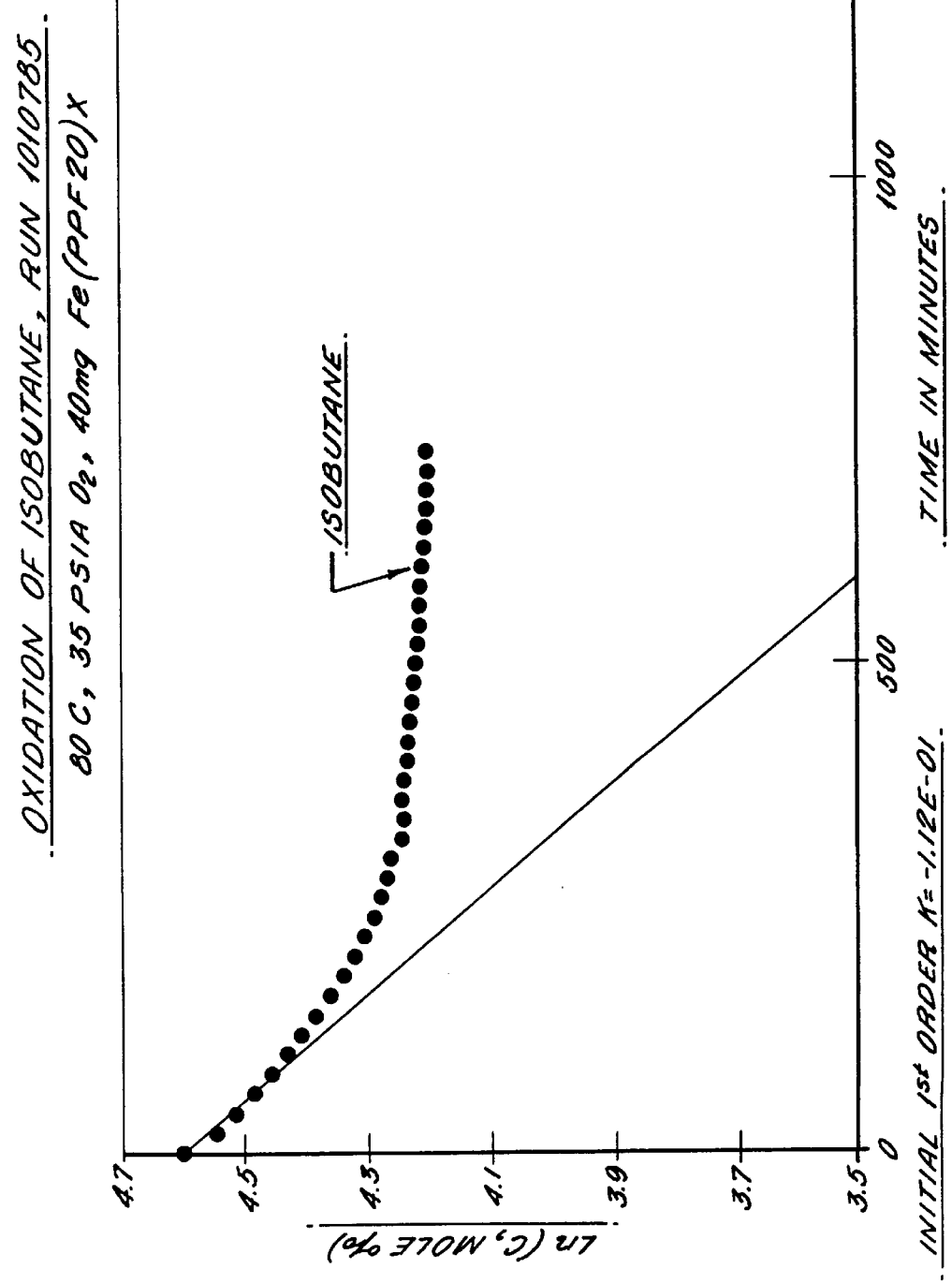

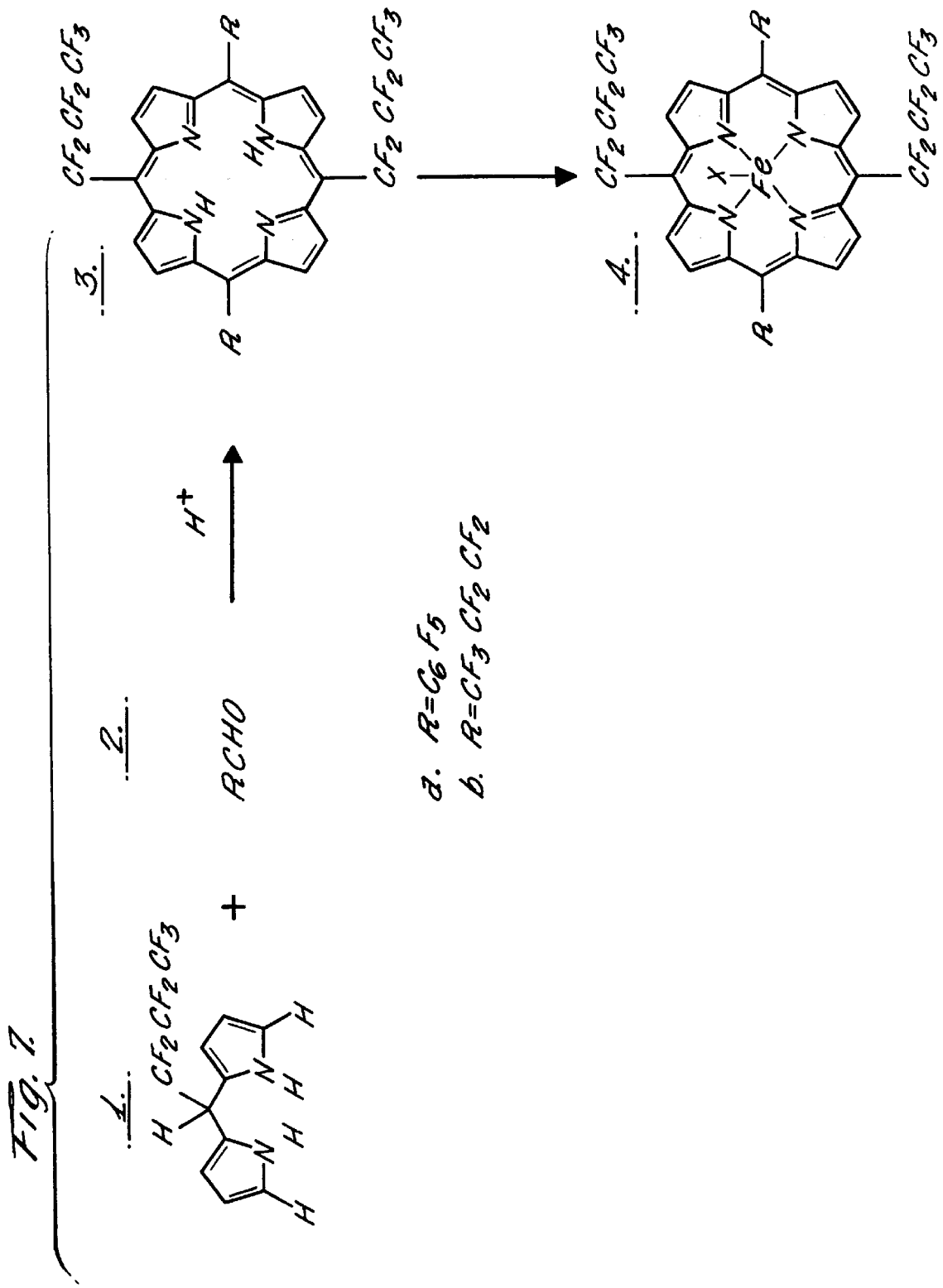

ALKANE OXIDATION WITH PORPHYRINS AND METAL COMPLEXES THEREOF HAVING HALOALKYL SIDE CHAINS

This is a divisional of applications Ser. No. 08/405,684 filed on Mar. 17, 1995, now patented as U.S. Pat. No. 5,608,054, which is a continuation-in-part of application Ser. No.08/174,732 filed Dec. 29, 1993, now U.S. Pat. No. 5,571,908 and which is a C.I.P. of application Ser. No. 08/175,057 filed Dec. 29, 1993 now abandoned.

The Government of the United States of America has rights in this invention pursuant to Cooperative Agreement No. DE-FC21-90MC26029 awarded by the U.S. Department of Energy.

BACKGROUND

Electron deficient metalloporphyrins are efficient catalysts for the highly selective air oxidation of light alkanes to alcohols, P. E. Ellis and J. E. Lyons, Cat. Lett., 3, 389, 1989; J. E. Lyons and P. E. Ellis, Catt. Lett., 8, 45, 1991; Lyons and Ellis, U.S. Pat. Nos. 4,900,871; 4,970,348, as well as for efficient decomposition of alkyl hydroperoxides, Lyons and Ellis, J. Catalysis, 141, 311, 1993; Lyons and Ellis, U.S. Pat. No. 5,120,886. They may be prepared by the co-condensation of pyrrole with the appropriate aldehyde, Badger, Jones and Leslett, Aust. J. Chem., 17, 1029, 1964; Lindsey and Wagner, J. Org. Chem., 54, 828, 1989; U.S. Pat. Nos. 4,970,348 and 5,120,882, followed by metal insertion, Adler, Longo, Kampos and Kim, J. Inorg. Nucl. Chem., 32, 2443, 1970, and β-halogenation, U.S. Pat. Nos. 4,892,941 and 4,970,348. Other patents disclosing use of metal coordination complex catalysts in oxidation of alkanes are Ellis et al U.S. Pat. Nos. 4,895,680 and 4,895,682.

Meso-tetrakis(perhaloalkyl)porphyrins, for example meso-tetra(trifluoromethyl)porphyrin, have been prepared by the self-condensation of the corresponding 2-hydroxy (perhalo-alkyl)pyrrole by prior activation of the hydroxy leaving group, Wijesekera, U.S. Pat. No. 5,241,062.

t-Butyl alcohol has been prepared by the catalytic decomposition of t-butyl hydroperoxide (TBHP), preferably in solution in t-butyl alcohol, in the presence of a metal phthalocyanine of a metal of Group IB, Group VIIB or Group VIIIB, for example chloroferric phthalocyanine and rhenium heptoxide-p-dioxane or oxotrichloro-bis (triphenylphosphine) rhenium, Sanderson et al U.S. Pat. No. 4,910,349.

t-Butylhydroperoxide may be decomposed to t-butyl alcohol using a metal porphine catalyst, for example tetraphenylporphine, optionally promoted with a thiol and a heterocyclic amine, Sanderson et al, U.S. Pat. No. 4,922,034, or using an imidazole-promoted phthalocyanine (PCY) catalyst, for example Fe(III)PCYCl or Mn(II)PCY or VOPCY, Sanderson et al U.S. Pat. No. 4,912,266.

Isobutane may be converted continuously to isobutyl alcohol by a process including the step of deomposing t-butylhydroperoxide to t-butyl alcohol, using a monocyclic solvent and a PCY decomposition catalyst, Marcquis et al U.S. Pat. No. 4,992,602.

t-Butylhydroperoxide may be decomposed to t-butyl alcohol using a metal porphine catalyst such as a trivalent Mn or Fe tetraphenylporphine, optionally promoted with an amine or thiol, or a soluble Ru catalyst promoted with a bidentate ligand such as $Ru(AcAc)_3$ promoted with bis(salicylidene) ethylenediamine, or a promoted PCY catalyst such as a Mn, Fe or vanadyl PCY promoted with an amine, a Re compound such as $NH_4ReO_4$, a mercaptan and a free radical inhibitor, a base or a metal borate, Derwent Abstract (Week 8912, Other Aliphatics, page 58) of reference 89-087492/12 (EP 308-101-A).

Hydroperoxides may be decomposed with metal ligand complexes in which hydrogen in the ligand molecule has been substituted with electron-withdrawing elements or groups, for example halogen or nitro or cyano group, Lyons et al U.S. Pat. No. 5,120,886, which is incorporated by reference herein,

OTHER PUBLICATIONS

S. G. DiMagno, R. A. Williams and M. J. Therien, "Facile Synthesis of meso-Tetrakis(perfluoroalkyl)porphyrins: Spectroscopic Properties and X-ray Crystal Structure of Highly Electron-Deficient 5,10,15,20-Tetrakis- (heptafluoropropyl)porphyrin.", J. Org. Chem. Vol. 59, No. 23, pp 6943–6948 1994.

M. J. Therien et al U.S. Pat. No. 5,371,199 issued Dec. 6, 1994 from an application filed Aug. 14, 1992, discloses meso-haloalkylporphyrins having 1 to 20 carbon atoms in at least one haloalkyl group, beta-haloalkylporphyrins having 2 to 20 carbon atoms in at least one haloalkyl group, beta-haloalkylporphyrins having 1 to 20 carbon atoms in at least five haloalkyl groups, and beta-haloarylporphyrins having 6 to 20 carbon atoms in at least five haloaryl groups.

Linear porphyrin arrays synthesized via reactions including $CF_3CHO$ + pyrrole to afford trifluoro dipyrromethane are disclosed in the abstract of a poster at the American Chemical Society Division of Organic Chemistry meeting in San Diego, Calif. Mar. 13–17, 1994 by R. W. Wagner, N. Nishino and J. S. Lindsey, "Building Block Synthesis of Linear-Amphipathic Porphyrin Arrays".

DESCRIPTION OF THE INVENTION

The invention comprises new compositions of matter having the structural formula:

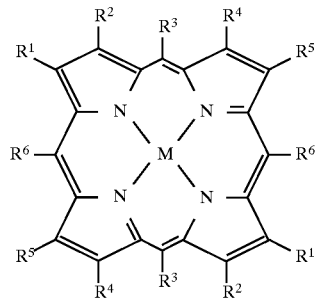

where M comprises a transition metal such as iron, manganese, cobalt, copper, ruthenium, chromium and the like, $R^3$ and $R^6$ comprise at least one halocarbyl group containing 2 to 8 carbon atoms, and $R^1$, $R^2$, $R^4$ and $R^5$ are independently hydrogen, hydrocarbyl, or electron-withdrawing substituents, for example halogen, nitro, cyano or halocarbyl. Anions such as azide, halide, hydroxide or nitride may be associated with the metal M. Porphyrins having the formula I include porphyrins comprising two or more meso-halocarbylporphyrins in dimeric or mu-oxo dimer forms or polymeric forms as known in the porphyrin art.

The compounds according to the invention are haloalkylporphyrins and metal complexes thereof containing in a meso position or positions at least one straight or branched chain haloalkyl group having 2 to 8 carbon atoms, and more preferably 3 to 6 carbon atoms, in the haloalkyl group.

Preferred haloalkyl groups in the porphyrins according to the invention are straight or branched chain heptafluoropropyl groups.

The porphyrins according to the invention may contain different halocarbyl groups in different meso positions, as in the compound, $[Fe(C_6F_5)_2(C_3F_7)_2P]_2O$, where P is porphyrin, $R^6$ in formula I is $C_6F_5$ and $R^3$ in formula I is $C_3F_7$, or may contain the same halocarbyl group in each of the substituted meso positions, as in the compound [Fe$(C_3F_7)_4P]_2O$, where P in Formula I is porphyrin, and $R^3$ and $R^6$ are each heptafluoropropyl.

CATALYST PREPARATION

The compounds according to the invention may be prepared for example by reaction of a halopropyl-substituted dipyrromethane such as bis(pyrrol-2-yl) heptafluoropropylmethane (FIG. 7, 1) with a meso-halopropyl-substituted aldehyde (FIG. 7, 2, R=$CF_2CF_2CF_3$) in the presence of a catalyst such as a solution of hydrobromic acid in acetic acid to obtain an intermediate porphyrinogen, followed by treatment of the intermediate porphyrinogen with 1,2-dichloro-5,6-dicyano-1,4-benzoquinone (DDQ) to produce meso-tetrakis (heptafluoropropyl)porphyrin (FIG. 7, 3b. The iron complex of meso-tetrakis(heptafluoropropyl)porphyrin is typically prepared by reaction of the meso-tetrakis (heptafluoropropyl)porphyrin with ferrous chloride in acetic acid and sodium acetate.

An acidic granular solid catalyst such as montmorillonite clay may be used as catalyst, instead of HBr-$CH_3COOH$, for the reaction of a dipyrromethane with an aldehyde to produce an intermediate porphyrinogen, with substantially improved results, for example twice the yield, over those obtained with HBr-$CH_3COOH$. Other known acidic granular solid catalysts may also be used, such as other acidic clays, acidic zeolites, solid superacids such as sulfated zirconia, and the like. Other known methods for preparing meso-halocarbylporphyrins may be adapted for the preparation of the meso-halocarbylporphyrins according to the invention, by a person skilled in the art in the light of the present specification.

OXIDATION PROCESSES

Transition metal complexes of the compositions according to the invention are highly effective catalysts for the oxidation of organic compounds. Generally, such catalysts are useful in those oxidations of organic compounds for which transition metal complexes of porphyrins, and particularly halogen-containing porphyrin structures are useful, as known in the art. See for example Lyons and Ellis U.S. Pat. Nos. 4,900,871 and 4,970,348 supra.

The oxidation, which may be carried out in a generally known manner, is desirably conducted in the liquid phase, although this is not critical, using such organic solvents as benzene, acetic acid, acetonitrile, methyl acetate, or like solvents which are inert to the conditions of the reactions, or in a neat solution of the hydrocarbon if it is liquid, and under pressures ranging from about 15 to 1500 psig, preferably 30 to 750 psig, at temperature of from about 25° to 250° C., preferably 70° to 180° C. Depending upon whether the hydrocarbon to be oxidized is a solid, liquid or gas, it is dissolved in or bubbled through the solvent, together with air or oxygen, in the presence of catalyst for periods of time sufficient to yield the desired oxidation product, generally from about 0.5 to 100 hours, and preferably from 1 to 10 hours.

The choice of solvent, while not critical, can have an effect on the rates and selectivities obtained and should be selected carefully in order to optimize the desired results. For example, solvents such as acetonitrile and acetic acid are often very effective for the oxidation of alkanes to form oxygen-containing compounds, whereas reactions carried out in solvents such as methyl acetate or benzene occur more slowly.

The ratios of the various reactants may vary widely, and are not critical. For example, the amount of catalyst employed can range from about $10^{-6}$ to $10^{-3}$ mole of catalyst per mole of hydrocarbon such as alkane, and more preferably from about $10^{-5}$ to $10^{-4}$ mole of catalyst per mole of hydrocarbon, although other amounts are not precluded; while the amount of oxygen relative to the hydrocarbon starting material may also vary widely, generally $10^{-2}$ to $10^2$ moles of oxygen per mole of hydrocarbon. Care should be taken since some of the ratios fall within explosive limits. As a group, the catalysts are almost always soluble unless used in high concentration. Thus, as a rule, the reactions are carried out homogeneously.

OXIDATION SUBSTRATE

The substrate for the process for oxidation of organic compounds, using the composition of the invention as catalyst may be an alkane such as methane, ethane, propane, n-butane, isobutane, n-pentane, isopentane, and the like, or an alkyl-substituted cyclic compound such as toluene, xylene, mesitylene and the like. Preferably but not necessarily, the substrate contains 1 to 10 carbon atoms in the molecule. Mixtures of compounds can be used.

HYDROPEROXIDE DECOMPOSITION PROCESSES

Transition metal complexes of the compositions according to the invention are highly effective catalysts for the decomposition of organic hydroperoxides. Generally, such catalysts are useful in those decompositions of organic hydroperoxides for which transition metal complexes of porphyrins, and particularly halogen-containing porphyrin structures are useful catalysts, as known in the art. See for example Lyons and Ellis U.S. Pat. No. 5,112,886 supra.

The hydroperoxide decomposition process according to the invention may be carried out in any known manner for decomposing hydroperoxides, using however the catalyst of the invention instead of the known catalysts of the prior art. The decomposition is preferably performed with the hydroperoxide dissolved in a suitable organic solvent, which may for example be the alcohol which is formed by the decomposition of the hydroperoxide. Any suitable temperature and pressure may be used, as known in the art for hydroperoxide decomposition processes. A preferred temperature is in the range from 25° to 125° C. Because of the rapid reaction rate of the catalysts used according to the invention, the reaction times may be fairly short, in the range from 0.1 to 5 hours, preferably 0.1 to 1 hour.

HYDROPEROXIDE DECOMPOSITION SUBSTRATE

Hydroperoxides which may be decomposed according to the invention include compounds having the formula ROOH, where R is an organic radical, typically a straight or branched chain alkyl or cycloalkyl group containing 2 to 15 carbon atoms, an aryl group such as a monocyclic or polycyclic group in which the cyclic groups may optionally be substituted with one or more substituents inert to the decomposition reaction, such as alkyl or alkoxy, containing 1 to 7 carbon atoms, nitro, carboxyl or carboxyl ester containing up to about 15 carbon atoms and a halogen atom such as chloride, bromide, or an alkaryl group in which the alkyl chain contains from 1 to 15 carbon atoms and the aryl group is as above described. Preferably R is an alkyl or cycloalkyl group containing 4 to 12 carbon atoms or an alkaryl group in which the aromatic moiety is phenyl and the alkyl substituent is straight or branched chain alkyl or cycloalkyl containing up to about 6 carbon atoms. Examples are t-butyl and isobutyl hydroperoxide, isoamyl hydroperoxide, 2-methylbutyl-2-hydroperoxide, cyclohexyl hydroperoxide, cyclohexylphenyl hydroperoxide, phenethyl hydroperoxide and cumyl hydroperoxide, the latter two of which are converted to phenethyl alcohol and cumyl alcohol, respectively.

DRAWINGS

FIG. 1 shows the mole % of reactant, isobutane (IC4), and product, tertiary butyl alcohol (TBA), as a function of time in the oxidation of isobutane at 80° C. and 35 psia $O_2$ using 32 mg of Fe[$PPF_{28}H_8$]X, where X is a halogen. FIG. 2 shows ln(C, mole %) of isobutane as a function of time in the same oxidation run.

FIG. 3 shows mole % of reactant and product as a function of time in the oxidation of isobutane in a second run at the same conditions and with the same catalyst as in the run of FIGS. 1 and 2. FIG. 4 shows ln(C, mole %) of isobutane as a function of time in the second run.

FIGS. 5 and 6 show the mole % of reactant and product and ln(C, mole %) of isobutane in a third run at 80° C. and 35 psia $O_2$ using 40 mg of the same catalyst as in the first and second runs.

FIG. 7 is a graphic depiction of reaction paths for production of a typical compound according to the invention.

EXAMPLES

Example 1

Preparation of 5,15-bis(heptafluoropropyl)-10,20-bis (pentafluorophenyl)porphyrin Equimolar quantities of bis(pyrrol-2-yl) heptafluoropropylmethane 1 and pentafluorobenzaldehyde (FIG. 7, 2a; R=$C_6F_5$) were heated at reflux for 10–20 h in degassed chloroform containing montmorillonite K10 clay as catalyst. The reaction mixture was treated with a solution of 2,3-dichloro-5,6-dicyano-1,4-benzoquinone (DDQ) in benzene and reflux continued for a further 20 h. The clay catalyst was removed by filtration and the desired porphyrin, 5,15-bis(heptafluoropropyl)-10,20-bis(pentafluorophenyl)-porphyrin [3a; R=$C_6F_5$); Fe($C_6F_5$)$_2$($C_3F_7$)$_2$$PH_2$; P=porphyrin] isolated by passing through neutral alumina and crystallization from dichloromethane/ methanol. MS(FAB): m/z=979 (M+1); UV: $\lambda_{max}$, 388 (Soret), 428 (sh), 560, 598 nm.

Example 2

Preparation of 5,10,15,20-tetrakis (heptafluoropropyl) porphyrin

The porphyrin 5,10,15,20-tetrakis(heptafluoropropyl)-porphyrin [FIG. 7, 3b; R=$C_3F7$; ($C_3F_7$)$PH_2$] was prepared as described in Example 1 using heptafluorobutyraldehyde (FIG. 7, 2b; as the hydrate) instead of pentafluorobenzaldehyde (FIG. 7, 2a). MS(FAB): m/z=984 (M+2); UV: $\lambda_{max}$, 404 (Soret), 508, 544, 590, 646 nm.

Example 3

Preparation of 5,15-bis(heptafluoropropyl)-10,20-bis (pentafluorophenyl)porphyrinatoiron The porphyrin FIG. 7, 3a prepared in Example 1 (400 mg) and sodium acetate (500 mg) were heated to near reflux in degassed acetic acid (200 mL) and treated with ferrous chloride (500 mg). The heating was continued for 30 min under argon and the solution was allowed to stir overnight at room temperature exposed to air. Hydrochloric acid (3M, 200 mL) was added, the solid filtered, washed with 1M hydrochloric acid and dried in a desiccator. The crude iron complex was redissolved in chloroform, extracted with 2M aqueous sodium hydroxide and passed through neutral alumina (15% water added), eluting with chloroform. The pure iron complex FIG. 7, 4a (R=$C_6F_5$) was isolated by evaporating the solvent. MS(FAB): 1032 (M-X); UV: $\lambda_{max}$, 388 (Soret), 428 (sh), 560, 598 nm.

Example 4

Preparation of 5,10,15,20-tetrakis (heptafluoropropyl)-porphyrinatoiron

The crude iron complex FIG. 7, 4b was prepared as described in Example 3 using the porphyrin FIG. 7, 3b prepared in Example 2. Purification was carried out by passing a chloroform solution through neutral alumina (15% water added) and the pure product isolated by evaporation of the solvent. MS(FAB): 1036 (M-X); UV: $\lambda_{max}$, 396 (Soret), 566, 600 nm.

Examples 5–11

Oxidation of isobutane using meso-perfluoropropylporphyrinatoiron catalysts

Isobutane was oxidized to tertiary butyl alcohol using meso-perfluoropropylporphyrinatoiron catalyst and conditions as set forth in footnote a to Table 1. Table 1 shows the results.

TABLE 1

Oxidation of Isobutane Using meso-Perfluoro-propyl Porphyrinato Iron Catalysts

| Complex | T,°C. | t, hrs | TO[b] | TBA Sel, %[c] |
|---|---|---|---|---|
| Fe(OEP)Cl | 60 | 6 | 0 | — |
| Fe(TPP)Cl | 60 | 6 | 0 | — |
| Fe[$C_6F_5$]$_4$P]Cl | 60 | 6 | 1100 | 90 |
| [Fe($C_6F_5$)$_2$($C_3F_7$)$_2$P]$_2$O | 60 | 6[d] | 90 | NA |
|  |  | 12 | 710 | 90 |
| [Fe($C_3F_7$)$_4$P]$_2$O | 60 | 6[e] | 110 | NA |
|  |  | 12 | 1110 | 81 |

[a]The catalyst, 0.013 mmole, was dissolved in 25 ml benzene to which 7.0 g i-$C_4H_{10}$ was added. Oxygen (to 100 psig) was added at reaction temperature and the mixture stirred for the designated time. Product analysis by glpc, gas liquid phase chromatography.
[b]Moles $O_2$ taken up/mole catalyst after reaction time
[c](moles tertiary butyl alcohol formed/moles i-$C_4H_{10}$ reacted) × 100
[d]Reaction had a 5 hour induction period.
[e]Reaction had a 3 hour induction period

Examples 12–14

TABLE 2

Decomposition of tert-butyl Hydroperoxide Catalyzed By meso-Perfluorocarbyl Porphyrinato Iron Complexes[a]

| Complex[d] | T, °C | \multicolumn{4}{c}{$O_2$ Evolution[b] in time t, hr} | $RO_2H$ Conv.[c] |
|---|---|---|---|---|---|---|
|   |   | 1 | 2 | 3 | 4 |   |
| A | 80 | 1300 | NA | NA | 1375 | 92.5% |
| B | 80 | 1000 | NA | 1300 | 1390 | 94% |
| C | 80 | 1130 | 1260 | 1325 | 1400 | >95% |
| D | 80 | 365 | 445 | 450 | 450 | 31% |

[a]The catalyst, 0.60 mg, was added directly to a stirred solution of tert-butyl hydroperoxide, 13.8 g, (dried thoroughly over activated 3A mole sieves prior to use) in tert-butyl alcohol, 18.1 g, at 80° C. Oxygen evolution was measured manometrically. Liquid products were analyzed by glpc before and after the runs.
[b]Oxygen evolved in cc's.
[c][(moles $RO_2H_{init}$ - moles $RO_2H_{final}$)/moles $RO_2H_{init}$] × 100
[d]A = $Fe[C_6F_5)_4P]Cl$
B = $[Fe(C_6F_5)_2(C_3F_7)_2P]_2O$
C = $[Fe(C_3F_7)_4P]_2O$
D = $[Fe(CF_3)P]_2O$

The invention claimed is:

1. Process for partially oxidizing alkanes which comprises contacting an alkane under partial oxidation conditions with oxygen and a catalyst comprising a compound having the following structural formula:

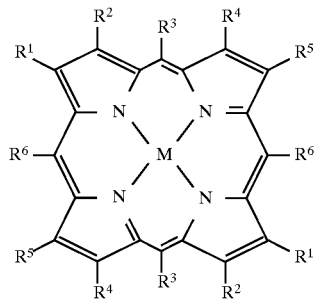

where M is transition metal with or without halide, hydroxide, azide or nitride associated therewith, and $R^3$ is hydrogen or halocarbyl and $R^6$ is hydrogen or halocarbyl, but $R^3$ and $R^6$ are not both hydrogen, $R^3$ and $R^6$ are not both the same halocarbyl, and at least one of said $R^3$ and $R^6$ is haloalkyl having 2 to 8 carbon atoms, and $R^1$, $R^2$, $R^4$ and $R^5$ are independently hydrogen, hydrocarbyl, halogen, nitro, cyano or halocarbyl; or polymeric forms thereof: to produce a partial oxidation product.

2. Process according to claim 1 wherein said first-named halocarbyl is haloalkyl group having 3 to 6 carbon atoms.

3. Process according to claim 2 wherein said first-named halocarbyl is heptahalopropyl group.

4. Process according to claim 3 wherein said first-named halocarbyl is heptafluoropropyl group.

5. Process according to claim 1 wherein said first-named halocarbyl is a straight chain haloalkyl group.

6. Process according to claim 1 wherein said first-named halocarbyl is a branched chain haloalkyl group containing 3 to 8 carbon atoms.

7. Process according to claim 1 wherein said first-named halocarbyl is a straight chain heptafluoropropyl, M is iron and $R^1$, $R^2$, $R^4$ and $R^5$ are hydrogen.

8. Process according to claim 1 wherein said alkane is isobutane and said partial oxidation product is t-butyl alcohol.

9. Process according to claim 1 wherein said alkane is cyclohexane and said partial oxidation product is a mixture of cyclohexanol and cyclohexanone.

10. Process according to claim 1 wherein said alkane is isopentane and said partial oxidation product is a mixture rich in t-amyl alcohol.

11. Process according to claim 1 wherein said alkane is propane and said partial oxidation product is a mixture of acetone and isopropyl alcohol.

12. Process according to claim 1 wherein said polymeric form of said catalyst comprises a porphyrin $\mu$-oxo dimer, where M is iron, and $R^3$ is heptafluoropropyl and $R^6$ is pentafluorophenyl, and $R^1$, $R^2$, $R^4$ and $R^5$ are independently hydrogen, hydrocarbyl, halogen, nitro, cyano or halocarbyl.

\* \* \* \* \*